(12) United States Patent
Bianchi

(10) Patent No.: US 9,056,149 B2
(45) Date of Patent: Jun. 16, 2015

(54) BODYBOARD WITH HULL AND PLANAR SECTIONS

(76) Inventor: Michael Bianchi, San Diego, CA (US)

(*) Notice: Subject to any disclaimer, the term of this patent is extended or adjusted under 35 U.S.C. 154(b) by 1594 days.

(21) Appl. No.: 12/202,082

(22) Filed: Aug. 29, 2008

(65) Prior Publication Data

US 2009/0120348 A1 May 14, 2009

Related U.S. Application Data

(60) Provisional application No. 60/968,839, filed on Aug. 29, 2007.

(51) Int. Cl.
*B63B 35/00* (2006.01)
*A61L 27/24* (2006.01)
*B63B 35/79* (2006.01)

(52) U.S. Cl.
CPC .............. *A61L 27/24* (2013.01); *A61L 2400/12* (2013.01); *A61L 2430/02* (2013.01); *A61L 2430/40* (2013.01); *B63B 35/7906* (2013.01)

(58) Field of Classification Search
USPC .......................................................... 441/65
IPC .................................. B63B 2035/7903,35/7906
See application file for complete search history.

(56) References Cited

U.S. PATENT DOCUMENTS

| | | | | |
|---|---|---|---|---|
| 3,270,707 A | * | 9/1966 | Rozanski | 440/87 |
| 4,028,761 A | * | 6/1977 | Taylor | 441/65 |
| 4,886,476 A | * | 12/1989 | Brocone et al. | 441/65 |
| 4,894,035 A | * | 1/1990 | Pia | 441/79 |
| 5,362,269 A | * | 11/1994 | Leach | 441/65 |

* cited by examiner

*Primary Examiner* — Stephen Avila
(74) *Attorney, Agent, or Firm* — Mintz Levin Cohn Ferris Glovsky and Popeo, P.C.

(57) ABSTRACT

An improved bodyboard and bodyboard shape are presented. The bodyboard includes both a hull section and a planar section formed in the bottom surface of the bodyboard. The bodyboard presented herein provides a hydrodynamically-shaped object that allows a rider to ride waves, typically in a prone or kneeling position on top of at least a portion of the bodyboard. The bodyboard provides the rider more control, speed and maneuverability, without adding substantially to costs to manufacture and maintain the bodyboard.

8 Claims, 1 Drawing Sheet

1(A) 1(B)

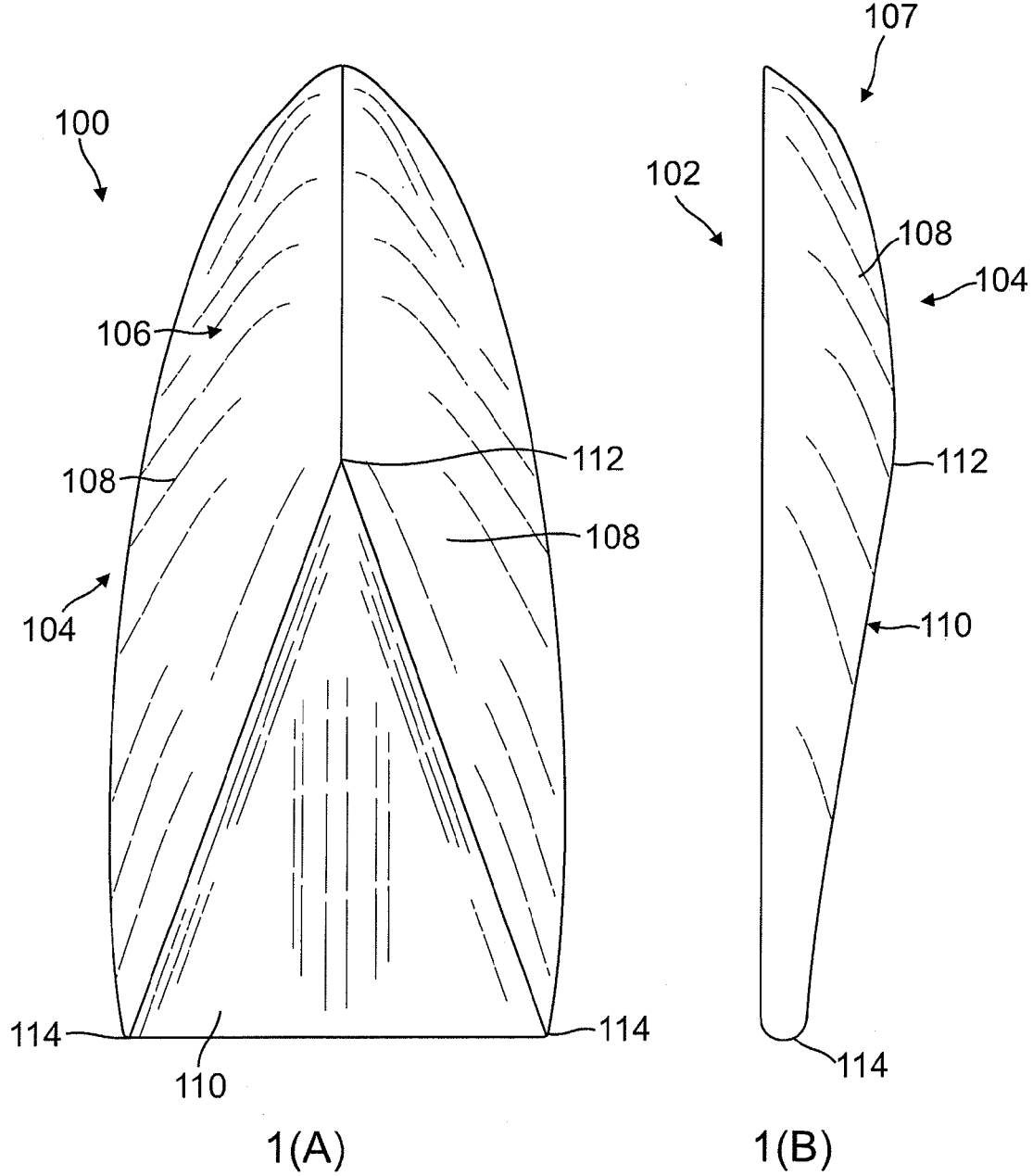

BODYBOARD WITH HULL AND PLANAR SECTIONS

CROSS-REFERENCED TO RELATED APPLICATIONS

This application claims the benefit of U.S. provisional patent application Ser. No. 60/968,839, filed on Aug. 29, 2007 and entitled "Bodyboard with Hull and Plannar Sections" which is incorporated by reference herein in its entirety.

BACKGROUND

Conventional bodyboards range from 38-42 inches in length, with a squared nose, angular rails (sides), and a tail which is crescent shaped, straight, or some variation of a "bat" tail. Conventional bodyboards also include an entirely planar bottom side, which in some bodyboards is only curved upwards toward the forward bow of the bodyboard. However, conventional bodyboards have limited maneuverability and steerability and speed.

SUMMARY

An improved bodyboard and bodyboard shape are presented. The bodyboard includes both a hull section and a planar section formed in the bottom surface of the bodyboard. The bodyboard presented herein provides a hydrodynamically-shaped object that allows a rider to ride waves, typically in a prone or kneeling position on top of at least a portion of the bodyboard. The bodyboard described herein provides the rider more control, speed and maneuverability, without adding substantially to costs to manufacture and maintain the bodyboard.

In implementation, a bodyboard includes buoyant lightweight material having a top surface to receive a rider, and a bottom surface having a forward bow section in the shape of a hull with longitudinally convex sides. The bottom surface flattens from a center point between the longitudinally convex sides of the hull toward aft corners of the bottom surface.

In another implementation, a bodyboard include a bottom surface having a forward bow section in the shape of a hull with longitudinally convex sides, the bottom surface including a planar section from a center point between the longitudinally convex sides of the hull toward aft corners of the bottom surface.

In yet another implementation, a bodyboard includes a top surface to receive a rider, and a bottom surface. The bottom surface has a forward bow section in the shape of a V-shaped hull that flattens from a center point between longitudinally convex sides of the V-shaped hull toward aft corners of the bottom surface to form a planar section.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

FIG. 1A depicts a bottom view of a bodyboard in accordance with some embodiments.

FIG. 1B depicts a side view of a bodyboard in accordance with some embodiments.

Like reference symbols in the various drawings indicate like elements.

DETAILED DESCRIPTION

This document describes a bodyboard, i.e. a hydrodynamically-shaped object that allows a rider to ride waves, typically in a prone or kneeling position on top of at least a portion of the bodyboard. The bodyboard described herein provides the rider more control, speed and maneuverability.

FIG. 1A is a bottom view and FIG. 1B is a side view of a bodyboard 100 that is formed of buoyant lightweight material. The bodyboard 100 includes a top surface 102 to receive a rider, and a bottom surface 104, which is depicted most clearly in FIG. 1A. The bottom surface 104 has a forward bow section 106 in the shape of a hull 107, with longitudinally convex sides 108. The bottom surface 104 also has a planar section 110, in which the bottom surface 104 flattens from a center point 112 between the longitudinally convex sides 108 of the hull 107 toward aft corners 114 of the bottom surface 104. The planar section 110 allows for low-drag movement without the need for substantial propulsion.

In some implementations, the hull 107 is a V-shaped hull, otherwise known as a V-bottom, that allows the bodyboard to cut through water, particularly at a low rate of speed, for greater maneuverability when a rider begins being pushed by a wave. The degree of angle of the V can be 2 to 45 degrees. However, the hull 107 can also be rounded so as to be adapted to roll with waves or other hydrodynamic effects. The planar section 110 is preferably triangular, and provides a planing surface for speed once a rider is catches the main energy of the wave and is moving at higher rates of speed. Accordingly, turning and the ability to perform tricks is enhanced by the hull 107, while the planar section 114 allows for high speed.

As stated above, the bodyboard 100 is formed of a lightweight buoyant material. The lightweight buoyant material can include a foam deck that defines the top surface 102. The foam deck can be composed of open or closed cell foam, or made of any other buoyant material. The foam deck can be encapsulated by a plastic bottom or other solid but flexible material. In some implementations, the foam of the foam deck can be polyethylene, arcel, or polypropylene. The plastic bottom can be surlyn or high density polyethylene. The foam deck and plastic bottom can encapsulate a foam core, which can be more rigid and/or buoyant than the foam deck. Each type of foam gives the bodyboard 100 a different amount of flex and control.

Although a few embodiments have been described in detail above, other modifications are possible. Other embodiments may be within the scope of the following claims.

The invention claimed is:

1. A bodyboard comprising:
   buoyant lightweight material comprising a top surface to receive a rider, and a bottom surface having a forward bow section in the shape of a hull with longitudinally convex sides, the bottom surface flattening from a center point between the longitudinally convex sides of the hull toward aft corners of the bottom surface to form a flat triangular surface.

2. A bodyboard in accordance with claim 1, wherein a vertical cross-section of the hull is V-shaped from the bow of the bodyboard and at least partly V-shaped with an increasingly wider flat bottom section from the center point to the aft corners of the bottom surface.

3. A bodyboard comprising a bottom surface having a forward bow section in the shape of a hull with longitudinally convex sides, the bottom surface including a planar section from a center point between the longitudinally convex sides of the hull toward aft corners of the bottom surface, the planar section being triangular along a horizontal axis and direction from the bow of the bodyboard to the aft corners of the stern of the bodyboard.

4. A bodyboard in accordance with claim 3, wherein a vertical cross-section of the hull is V-shaped from the bow of the bodyboard and at least partly V-shaped with an increasingly wider flat bottom section from the center point to the aft corners of the bottom surface.

5. A bodyboard in accordance with claim 3, further comprising a plastic underside that forms at least part of the bottom surface.

6. A bodyboard comprising:
   a top surface to receive a rider; and
   a bottom surface having a forward bow section with a vertical cross-sectional shape of a V-shaped hull that flattens on the bottom surface from a center point between longitudinally convex sides of the V-shaped hull toward aft corners of the bottom surface to form a triangular planar section along a horizontal axis and direction from the bow of the bodyboard to the aft corners of the stern of the bodyboard.

7. A bodyboard in accordance with claim 6, further comprising a foam deck that forms the top surface.

8. A bodyboard in accordance with claim 6, further comprising a plastic layer that forms the bottom surface.

* * * * *